US012535446B2

(12) United States Patent
Khan et al.

(10) Patent No.: US 12,535,446 B2
(45) Date of Patent: Jan. 27, 2026

(54) CAPACITIVE CHIP DETECTOR

(71) Applicant: PRATT & WHITNEY CANADA CORP., Longueuil (CA)

(72) Inventors: Sarmad Khan, Mississauga (CA); Daniel Arnone, Burlington (CA)

(73) Assignee: PRATT & WHITNEY CANADA CORP., Longueuil (CA)

(*) Notice: Subject to any disclaimer, the term of this patent is extended or adjusted under 35 U.S.C. 154(b) by 306 days.

(21) Appl. No.: 18/201,439

(22) Filed: May 24, 2023

(65) Prior Publication Data

US 2024/0393283 A1 Nov. 28, 2024

(51) Int. Cl.

| | |
|---|---|
| ***G01N 27/22*** | (2006.01) |
| ***F01D 21/00*** | (2006.01) |
| ***F01D 25/18*** | (2006.01) |
| ***F02C 7/06*** | (2006.01) |
| ***G01N 33/28*** | (2006.01) |

(52) U.S. Cl.

CPC ......... *G01N 27/226* (2013.01); *F01D 21/003* (2013.01); *F01D 25/18* (2013.01); *F02C 7/06* (2013.01); *G01N 33/2858* (2013.01); *G01N 33/2888* (2013.01); *F05D 2260/83* (2013.01)

(58) Field of Classification Search

None

See application file for complete search history.

(56) References Cited

U.S. PATENT DOCUMENTS 5,118,410 A * 6/1992 Rumberger ........ G01N 15/0656 210/243
5,164,675 A 11/1992 Howe et al.
5,604,441 A 2/1997 Freese
6,850,865 B2 2/2005 Hirthe
7,129,715 B2 10/2006 Hayashi et al.
8,522,604 B2 9/2013 Zhe et al.
10,197,488 B2 2/2019 Youssef
10,254,210 B2 4/2019 Weiser
10,317,354 B2 6/2019 Ricci (Continued)

FOREIGN PATENT DOCUMENTS

DE 10000148 A1 7/2001
WO WO-2008074559 A1 * 6/2008 ............. G01N 27/22

OTHER PUBLICATIONS

Han, Zhibin, Yishou Wang, and Xinlin Qing. "Characteristics study of in-situ capacitive sensor for monitoring lubrication oil debris." Sensors 17.12 (2017): 2851.*

(Continued)

*Primary Examiner* — Herbert K Roberts

(74) *Attorney, Agent, or Firm* — Norton Rose Fulbright Canada LLP

(57) ABSTRACT

Capacitive chip detectors for detecting metallic chips in engine fluid of an engine are provided. A capacitive chip detector includes a capacitor having first and second electric conductors. The detector further includes an inlet for receiving engine fluid between the first and second electric conductors. The capacitive chip detector includes an electric circuit including the capacitor, which capacitance changes when metallic chips are present between the first and second electric conductors. The electric circuit provides an output indicative of a chip detection between the first and second electric conductors.

15 Claims, 4 Drawing Sheets

(56) References Cited

U.S. PATENT DOCUMENTS

| | | | |
|---|---|---|---|
| 10,705,038 B2 | 7/2020 | Ricci | |
| 11,061,010 B2 | 7/2021 | Wang et al. | |
| 11,740,222 B2 | 8/2023 | Cosoleto et al. | |
| 11,906,504 B2 | 2/2024 | Szczesnowicz et al. | |
| 12,085,556 B2 | 9/2024 | Haye et al. | |
| 12,203,920 B2 | 1/2025 | Riverin | |
| 12,210,010 B2 | 1/2025 | Coupard et al. | |
| 2015/0075268 A1 | 3/2015 | Qi | |
| 2016/0370275 A1* | 12/2016 | Weiser | B03C 1/282 |
| 2023/0054919 A1 | 2/2023 | Al-Khairy | |

OTHER PUBLICATIONS

Wang, Yishou, et al. "In-situ capacitive sensor for monitoring debris of lubricant oil." Industrial Lubrication and Tribology 70.7 (2018): 1310-1319.*

Wang et al, In-situ capacitive sensor for monitoring debris of lubricant oil, Industrial Lubrication and Tribology 70/7 (2018) 1310-1319, Emerald Publishing Limited, ISSN 0036-8792, China.

European Patent Office, Communication re. extended European search report for European patent application No. 24177701, filed Nov. 8, 2024.

* cited by examiner

CAPACITIVE CHIP DETECTOR

TECHNICAL FIELD

The disclosure relates generally to health monitoring of engines, and more particularly to detecting chips in fluids of aircraft engines.

BACKGROUND

A magnetic chip detector is commonly found in a lubrication system of an aircraft engine to detect the presence of metallic chips in the lubricating fluid. The chip detector is immersed in the lubricating fluid so as to be exposed to the chips carried by the lubricating fluid. The presence of chips in the lubricating fluid may indicate a developing and/or impending mechanical problem exhibiting excessive wear of one or more components of the aircraft engine interacting with the lubrication system. The presence of metal chips in engine fluid can be indicative of a deteriorating engine health condition and it is desirable to improve chip detection in aircraft engines.

SUMMARY

In one aspect, the disclosure describes a capacitive chip detector for detecting chips in engine fluid of an engine. The capacitive chip detector comprises:

- a capacitor including:
- a first electric conductor having a first polarity;
- a second electric conductor having a second polarity opposite the first polarity, the first electric conductor being spaced apart from the second electric conductor; and
- an electric field between the first electric conductor and the second electric conductor;
- an inlet for receiving the engine fluid between the first electric conductor and the second electric conductor; and
- an electric circuit including the capacitor, the electric circuit providing an output indicative of a change in capacitance of the capacitor caused by a presence of one or more chips between the first electric conductor and the second electric conductor.

In another aspect, the disclosure describes an aircraft engine comprising:

- a lubrication system for distributing lubricating fluid to one or more lubrication loads; and
- a capacitive chip detector for detecting one or more chips carried by the lubricating fluid, the capacitive chip detector including:
- a cylindrical capacitor including:
- an electrically conductive inner cylinder having a first polarity;
- an electrically conductive outer cylinder having a second polarity opposite the first polarity, the outer cylinder surrounding the inner cylinder and being radially spaced apart from the inner cylinder; and
- an electric field between the inner cylinder and the outer cylinder;
- an inlet for receiving the lubricating fluid between the inner cylinder and the outer cylinder; and
- an electric circuit including the cylindrical capacitor, the electric circuit providing an output indicative of a change in capacitance of the cylindrical capacitor caused by an arrival of one or more chips between the inner cylinder and the outer cylinder.

In a further aspect, the disclosure describes a method of detecting metallic chips in engine fluid of an aircraft engine using a capacitive chip detector including a capacitor defined by a first electric conductor having a first polarity and a second electric conductor having a second polarity opposite the first polarity, the first electric conductor being spaced apart from the second electric conductor, the method comprising:

- receiving the engine fluid in an electric field between the first electric conductor and the second electric conductor; and
- using an electric circuit including the capacitor, generating an output indicative of a change in capacitance of the capacitor caused by a presence of one or more chips between the first electric conductor and the second electric conductor.

Further details of these and other aspects of the subject matter of this application will be apparent from the detailed description included below and the drawings.

DESCRIPTION OF THE DRAWINGS

Reference is now made to the accompanying drawings, in which.

DETAILED DESCRIPTION

Figure 1:
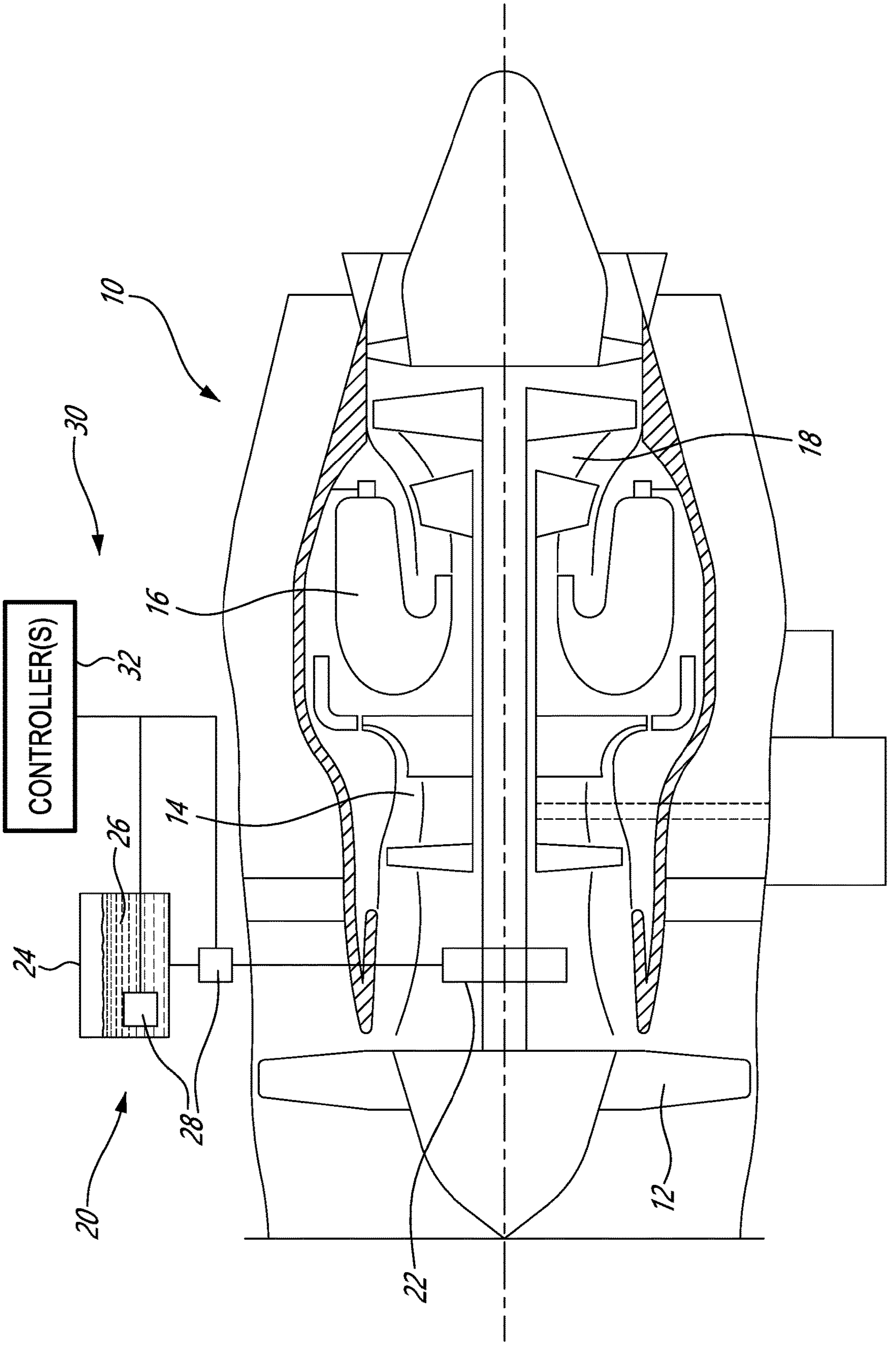
FIG. 1 is a schematic axial cross-section view of a turbofan gas turbine engine including a capacitive chip detector as described herein.

The present disclosure relates to systems and methods for detecting metallic chips in engine fluids (e.g., coolant, liquid fuel, lubricating fluid such as oil). In some embodiments, the systems and methods described herein may help assess a condition of an engine by using one or more chip detectors and/or collectors to reduce the probability of generating nuisance chip detections and associated annunciations or alarms. For example, the systems and methods described herein may reduce the probability of nuisance chip detections associated with the accumulation of acceptable smaller/fine magnetic debris/particles, commonly referred to as "fuzz" at a chip detector immersed in engine fluid. Some fuzz can be generated during the normal operation of an aircraft engine and may not necessarily be indicative of a developing or impending mechanical problem. For example, such fuzz can normally be generated during the initial period (e.g., a few hundred hours) of operation of an aircraft engine following initial entry into service or following extensive maintenance such as an overhaul. This initial period is also known as the engine's "break-in" period. Chip detections caused by the accumulation of the acceptable and relatively harmless fuzz, during the break-in period for example, oppose the design intent of the chip detector and are undesirable since they do not provide an accurate indication of a possible developing or impending problem.

Metallic chips that are carried by the engine fluid may be from metallic engine parts such as gear teeth or bearings, for example. Some disc type magnetic chip detectors use one disk-shaped magnet placed in a non-conductive and non-magnetically permeable isolator with two conductive steel end caps which, in combination, create a single chip capture zone. When a metallic chip of a sufficient size is attracted to the capture zone by the magnet, the metallic chip bridges (e.g., short-circuits) the gap between the steel end caps to complete an electric circuit that includes the gap. A controller or other annunciation circuitry connected to the magnetic chip detector may detect this change in resistance caused by the metallic chip and indicate to a pilot of the aircraft via a cockpit indication the presence of one or more magnetic chips having been detected by the magnetic chip detector.

Magnetic chip detectors may use rare earth magnets that provide a relatively high capture efficiency. This can result in a high sensitivity of a magnetic chip detector, which may increase the probability of nuisance detections. For example, a magnetic chip detector with a single capture zone may function as an on/off switch and may trigger an annunciation based on a relatively harmless single metallic filament having been captured in the single capture zone. Once the chip detection is triggered by one or more chips, the pilot may be required to abort the mission mid-flight, return to the ground (e.g., base) as soon as possible, and remove (or have maintenance personnel remove) the magnetic chip detector for visual inspection. The visual inspection verifies whether significant debris has been collected by the magnetic chip detector and hence whether maintenance is required before the aircraft can be dispatched again. If the detection is triggered by an insignificant metallic filament or other insignificant metallic particle(s), such detection can be a nuisance to the pilot and/or aircraft operator.

In some embodiments, the chip detectors described herein may reduce the probability of single chip detections and other nuisance detection events. In some embodiments, the chip detectors described herein may reduce the probability of fuzz-induced nuisance detections. In some embodiments, the chip detectors described herein may provide an indication of a degree of contamination that allows a system to discriminate between harmless/tolerable contamination and gross contamination indicative of a developing and/or impending mechanical problem. In some embodiments, the chip detectors described herein may provide an ability to discriminate between small or large chips being detected.

Aspects of various embodiments are described through reference to the drawings. Even though the description below is provided in relation to lubricating fluid, it is understood that some embodiments of the chip detectors, systems and methods described herein may also be used on other types of engine fluids such as engine coolant and liquid fuel for example.

The term "connected" may include both direct connection (in which two elements that are connected to each other contact each other) and indirect connection (in which at least one additional element is located between the two elements).

The term "substantially" as used herein may be applied to modify any quantitative representation which could permissibly vary without resulting in a change in the basic function to which it is related.

FIG. 1 is a schematic axial cross-section view of aircraft engine 10 (referred hereinafter as "engine 10") of a turbofan gas turbine engine preferably provided for use in subsonic flight, generally comprising, in serial flow communication, fan 12 through which ambient air is propelled, multistage compressor 14 for pressurizing the air, combustor 16 in which the compressed air is mixed with fuel and ignited for generating an annular stream of hot combustion gases, and turbine section 18 for extracting energy from the combustion gases. Engine 10 may be mounted to an aircraft and used to propel such aircraft. Even though FIG. 1 shows engine 10 being of the turbofan type, it is understood that aspects of the present disclosure are also applicable to other (e.g., turboshaft, turboprop, piston) types of aircraft engines.

Engine 10 may include lubrication (and/or other fluid) system 20 shown schematically and partially in FIG. 1. Lubrication system 20 may serve to lubricate, cool and clean one or more lubrication loads 22 such as bearings and gears of engine 10. Lubrication system 20 may include tank 24 and other components such as one or more pumps, one or more valves, and one or more filters. Tank 24 may be a reservoir containing a supply of lubricating fluid 26 such as oil for use by lubrication system 20. Lubrication system 20 may include one or more capacitive chip detectors (CCDs) 28. For example, lubrication system 20 may include a single CCD 28 or a plurality of CCDs 28 disposed at different locations within lubrication system 20. CCD 28 may be at least partially immersed in lubricating fluid 26 during operation. For example, CCD 28 may be disposed inside tank 24, inside a gearbox, or in a scavenge line.

CCD 28 may be part of chip detection system 30 (referred hereinafter as "system 30") and may be associated with and/or may be part of engine 10. System 30 may include controller 32 or other detection circuitry operatively connected to CCD 28. In various embodiments, controller 32 may include or form part of a Full Authority Digital Engine Control (FADEC) which may, for example, include one or more digital computer(s) or other data processors, sometimes referred to as electronic engine controller(s) (EEC) and related accessories that control at least some aspects of performance of engine 10. Controller 32 may, for example, be configured to make decisions regarding the control of engine 10. Controller 32 may include one or more data processors and non-transitory machine-readable memory. Controller 32 may receive input(s) from CCD 28, perform one or more procedures or steps defined by instructions stored in the memory to generate output(s) such as triggering a suitable annunciation to a pilot of the aircraft for example. Various aspects of the present disclosure may be embodied as systems, devices, methods and/or computer program products.

Figure 2B:
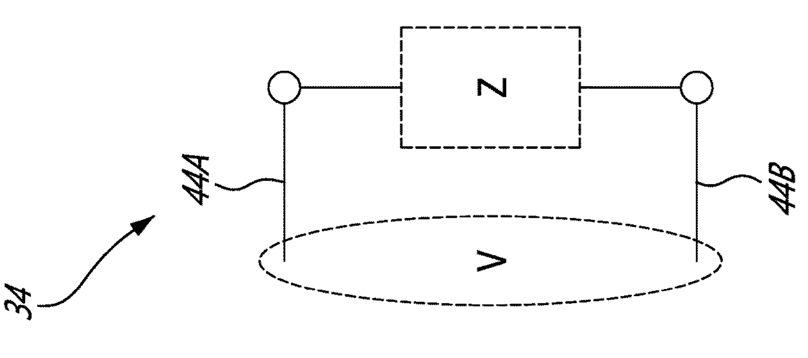
FIG. 2B is a schematic representation of an electric circuit associated with the capacitive chip detector of FIG. 2A.
Figure 2A:
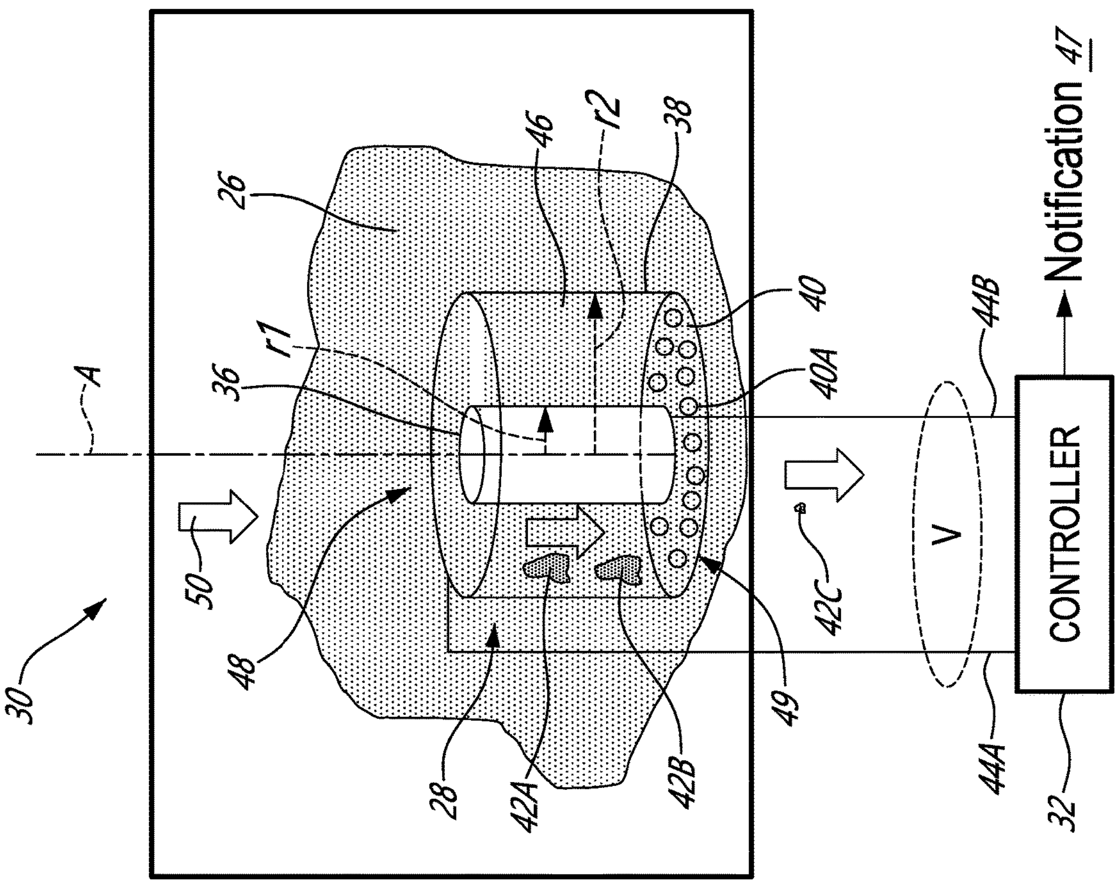
FIG. 2A is a schematic representation of an example capacitive chip detector of the engine of FIG. 1.

FIG. 2A is an exemplary schematic representation of CCD 28 shown as part of chip detection system 30 of engine 10. In some embodiments, CCD 28 includes a capacitor having first and second electric conductors separated by a dielectric. In some embodiments, the first and second electric conductors may be flat or curved plates that are spaced apart. As depicted in FIG. 2A, the capacitor of CCD 28 may have a cylindrical configuration where the first conductor is inner cylinder 36 and the second conductor is outer cylinder 38 surrounding inner cylinder 36. Inner cylinder 36 and outer cylinder 38 may be radially spaced apart to define a fluid-receiving gap (e.g., space 46) therebetween. Inner cylinder may have a radius $r_1$, and outer cylinder may have a radius 2. In some embodiments, inner cylinder 36 and outer cylinder 38 are concentric or coaxial about axis A. In some embodiments, inner cylinder 36 and outer cylinder 38 may have different or opposite polarities, such that a circumferential electric field is created by the separation of charge by a dielectric or non-conductive material or space 46 between inner cylinder 36 and outer cylinder 38. In some embodiments, inner cylinder 36 may be positively charged.

In some embodiments, outer cylinder 38 may be grounded. In still other embodiments, outer cylinder 38 may be negatively charged.

Although various embodiments described herein refer to CCD 28, 328 including a cylindrical capacitor having inner cylinder 36 and outer cylinder 38, it is contemplated that some embodiments may feature other geometric configurations for CCD 28, 328. For example, CCD 28, 328 may have a box-shaped (or cuboid) configuration in which the capacitor is defined by two flat conductive plates (e.g. inner and outer plates) separated by a dielectric.

In some embodiments, CCD 28 includes an inlet 48 for receiving lubricating fluid 26 which is travelling in direction 50 through space 46 between inner cylinder 36 and outer cylinder 38. Although various example embodiments described herein relate to lubricating fluid, it is contemplated that fluids may also include, for example, coolant and liquid fuels. In some embodiments, CCD 28 includes a strainer 40 at outlet 49 of CCD 28 which is downstream from inlet 48. As depicted, in some embodiments, strainer 40 may include one or more apertures 40A for allowing lubricating fluid 26 to exit outlet 49 of CCD 28. In some embodiments, the streamwise direction of system 30 is inlet 48 upstream, outlet 49 downstream of inlet 48, with the capacitor of CCD 28 located between inlet 48 and outlet 49. In some embodiments, a directional (e.g., one-way) valve may be disposed proximal to inlet 48. The directional valve may be configured to prevent the back flow of lubricating fluid 26 in a direction opposite to direction 50 to help retain chips 42A that have been collected in CCD 28.

In some embodiments, apertures 40A may have a uniform shape and/or size. In some embodiments, apertures 40A may have varying shapes and/or sizes. In some embodiments, apertures 40A may be sized so as to allow passage of chips 42C which are smaller than a predetermined threshold particle size (e.g. fuzz), while preventing passage of chips 42A, 42B which are larger than the predetermined threshold size (and therefore may be indicative of deteriorating engine components), thereby causing chips 42A, 42B to accumulate within CCD 28 over time. In some embodiments, strainer 40 may be made from a non-conductive material so as to reduce the likelihood of an electrical connection being formed between the inner cylinder 36 and outer cylinder 38.

Although FIG. 2A depicts strainer 40 as including one or more apertures 40A, it is contemplated that in other embodiments, strainer 40 may include a mesh with a selected mesh size configured to allow passage of lubricating fluid 26 and chips 42C which are smaller than the mesh size (e.g. fuzz), and prevent passage of chips 42A, 42B which are larger than the mesh size.

It will be appreciated that as CCD 28 includes two conductively charged cylinders separated by an insulator, CCD 28 is a cylindrical capacitor. The capacitance, C, of a cylindrical capacitor is $$C = \frac{2\pi\varepsilon L}{\ln\left(\frac{r_2}{r_1}\right)},$$

Where L Is the length of the cylinder, $r_2$ is the radius of the outer cylinder, $r_1$ is the radius of the inner cylinder, and ε is the permittivity of free space.

As lubricating fluid 26 passes through CCD 28, some chips 42A may be prevented from passing through strainer 40. Over time, such chips 42A, 42B may accumulate within dielectric space 46 of CCD 28, and may be expected not to escape from CCD 28 due to lubricating fluid 26 moving in direction 50 towards strainer 40. When chips 42A, 42B are metallic (or any material which conducts electricity), the accumulation of conductors within dielectric space 46 will affect the permittivity & of CCD 28. Given that the length and the radii of inner cylinder 36 and outer cylinder 38 are constants, a change in the permittivity of CCD 28 will result in a change in the capacitance of CCD 28. For example, a build-up of conducting (e.g. metallic) chips would be expected to decrease the capacitance of CCD 28, whereas a build-up of insulating chips (e.g. sand and dust) would be expected to increase the capacitance of CCD 28. In some embodiments, the inclusion of a directional (e.g., one-way) valve disposed upstream of CCD 28 may prevent one or more accumulated conducting chips from escaping the confines of space 46 between inner cylinder 36 and outer cylinder 38.

When an AC current or voltage with a frequency f is applied to a capacitor, the reactance of the capacitor (i.e., the resistance to alternating current) is given by $X=1/2\pi fC$ for an ideal capacitor. For an ideal capacitor, the magnitude of the total impedance, Z, is given by $|Z|=X$. For a non-ideal capacitor with a non-zero resistance, the total impedance, Z, is given by $Z=R+jX$, and the total magnitude of impedance is given by $$|Z| = \sqrt{R^2 + X^2}.$$

In some embodiments, as metallic chips 42A, 42B accumulate within space 46 of CCD 28, the resulting decrease in the capacitance of CCD 28 will result in a corresponding increase in the reactance of CCD 28, assuming the frequency of the voltage or current applied is kept constant. This property of CCD 28 may be advantageously used to detect the arrival and/or presence of metallic chips 42A, 42B between inner cylinder 36 and outer cylinder 38 of CCD 28.

In some embodiments, CCD 28 may form part of an electric circuit 34 which may include first output terminal 44A and second output terminal 44B together defining a single interface between CCD 28 and controller 32. As shown in FIG. 2B, the total impedance of CCD 28 may be represented as a component with impedance Z. In some embodiments, an alternating current or voltage may be applied across CCD 28 and the voltage across CCD 28 may be measured by, or transmitted to, controller 32. The magnitude of the voltage drop across CCD 28 may serve as a single output for controller 32 to use as an indication of whether or not a chip detection has occurred at CCD 28 and whether a notification 47 is warranted for further investigation and/or inspection and/or repair.

For example, if an AC voltage with a constant frequency is applied to circuit 34, in the absence of metallic chips 42A, 42B within CCD 28, a reference potential difference across CCD 28 may be established. As metallic chips 42A, 42B subsequently begin to accumulate in space 46 due to strainer 40 preventing the movement of chips exceeding a threshold size, the resulting decrease in capacitance of CCD 28 will cause an increase in reactance and total impedance, thereby resulting in an increase in the voltage across CCD 28 relative to the reference potential difference. In some embodiments, a threshold difference for the potential difference across CCD 28 relative to the reference potential difference in the absence of metallic chips 42A, 42B may be defined or otherwise set. When the difference in the voltage drop across CCD 28 exceeds the reference value by more than this threshold amount, controller 32 may be configured to sent an alert or notification 47 to draw attention to the possible need for maintenance or inspection for engine.

Accordingly, a chip detection at CCD 28 may be detected by way of a change in potential difference V across the cylindrical capacitor, which may be determined at controller 32. Upon detection of the change in potential difference V that is indicative of a legitimate chip detection, controller 32 may initiate notification 47 which may alert a pilot of the aircraft and/or another interested party. Notification 47 may be visual (e.g., indicator light or message) or aural (e.g., tone or spoken message).

Advantageously, the likelihood of alerts being triggered when unnecessary (so-called "false alarms") may be reduced given that the mesh size or aperture 40A size for strainer 40 may be selected so as to allow chips which are smaller in size (e.g. fuzz) to pass through strainer 40. Allowing fuzz to pass through strainer 40 may reduce the likelihood of metallic fuzz particles accumulating within space 46 (which may eventually result in a sufficient accumulation of metallic fuzz to result in the capacitance of CCD 28 falling sufficiently to trigger controller 32 to signal an alert).

It may be further appreciated that in some embodiments, CCD 28 need not involve the use of magnets to attract chips 42. In other words, CCD 28 may be devoid of magnets. While other types of detectors may rely on the use of magnets to attract metallic chips 42 to "bridge" gaps between conductors to establish the presence of chips 42, the CCD 28 instead relies on changes in capacitance rather than the establishment of any physical electrical connection by chips 42. As such, CCD 28 may alleviate common problems associated with the use of magnetic chip detectors, such as the oversensitivity of magnets used (resulting in too many chips being attracted, including fuzz), and the inability to both determine the size of particles being captured, as well as the inability to distinguish between the physical size of chips 42 being captured.

In various embodiments disclosed herein, the single potential difference value V may provide a single and informative input to controller 32 and allow controller 32 to determine the state of CCD 28. For example, potential difference value V may be the sole piece of information transferred from CCD 28 to controller 32. Controller 32 may then use potential difference value V with one or more rules available to controller 32 to determine whether notification 47 or other action is warranted. The rules may include actions associated with predetermined values for potential difference value V or predetermined ranges of values for potential difference V. The rules and the mesh size and/or aperture 40A size may be selected to provide a sensitivity suitable for providing legitimate chip detections and notifications 47.

The use of the single input may also facilitate integration of some embodiments of CCD 28 disclosed herein with new or existing aircraft engines. For example, the retrofitting of CCD 28 into engine 10 may require little to no hardware modifications, but may require software modifications to apply rules and carry out desired actions based on potential difference value V.

Figure 3B:
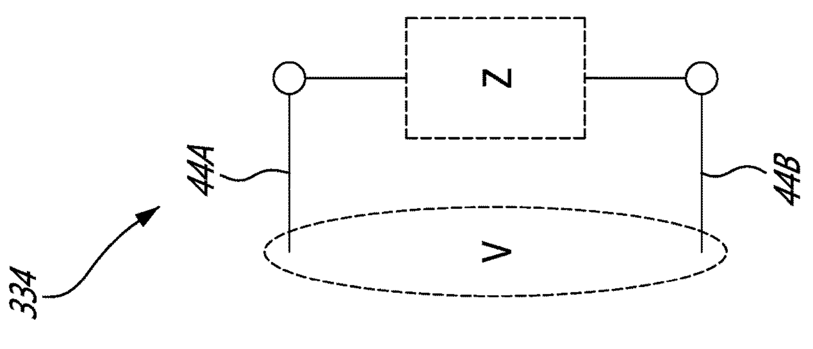
FIG. 3B is a schematic representation of an electric circuit associated with the capacitive chip detector of FIG. 3A.
Figure 3A:
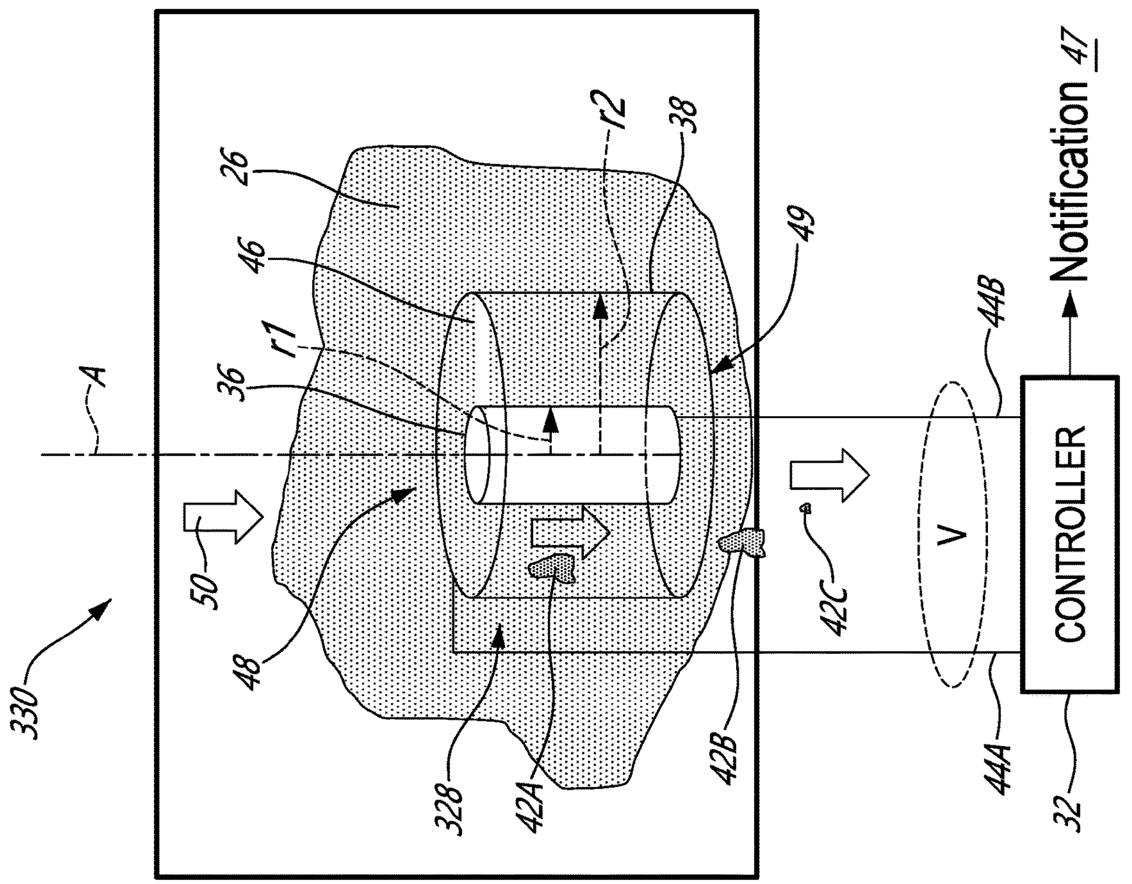
FIG. 3A is a schematic representation of an example capacitive chip detector of the engine of FIG. 1, in accordance with some embodiments.

FIG. 3A is a schematic representation of an example CCD 328, in accordance with some embodiments, shown as part of chip detection system 330 of engine 10. As depicted, CCD 328 is a cylindrical capacitor similar to CCD 28, and includes an inner cylinder 36 and an outer cylinder 38. Inner cylinder 36 may have a radius $r_1$, and outer cylinder 38 may have a radius $r_2$. In some embodiments, inner cylinder 36 and outer cylinder 38 are concentric or coaxial about axis A. In some embodiments, inner cylinder 36 and outer cylinder 38 may have different or opposite polarities, such that a circumferential electric field is created by the separation of charge by a dielectric or non-conductive material or space 46 between inner cylinder 36 and outer cylinder 38. In some embodiments, inner cylinder 36 may be positively charged. In some embodiments, outer cylinder 38 may be grounded. In still other embodiments, outer cylinder 38 may be negatively charged.

In some embodiments, CCD 328 includes an inlet 48 for receiving lubricating fluid 26 which is travelling in direction 50. As depicted, CCD 328 does not include any strainer or collection system at an outlet 49 of CCD 328. In some embodiments, the streamwise direction of system 330 is inlet 48 upstream, outlet 49 downstream of inlet 48, with the capacitor of CCD 328 located between inlet 48 and outlet 49. As such, CCD 328 may allow passage of substantially all chips 42A, 42B, 42C, irrespective of the size of the chips. As such, there is no accumulation of metallic chips in CCD 328 as lubricating fluid 26 flows through CCD 328.

As with CCD 28, CCD 328 includes two conductively charged cylinders separated by an insulator and as such is a cylindrical capacitor. The capacitance, C, of CCD 328 is $$C = \frac{2\pi\varepsilon L}{\ln\left(\frac{r_2}{r_1}\right)},$$

where L is the length of the cylinder, $r_2$ is the radius of the outer cylinder 38, $r_1$ is the radius of inner cylinder 36, and $\varepsilon$ is the permittivity of free space.

In contrast to the operation of CCD 28, as lubricating fluid 26 passes through CCD 328, substantially no chips 42A will be prevented from passing from the inlet 48 to outlet 49 of CCD 328. As such, it is not expected that the capacitance of CCD 328 will decrease over time, as metallic chips will not be accumulating within space 46 (depicted as chip 42B exiting CCD 328 in FIG. 3A). Nevertheless, when chips 42A, 42B, 42C are metallic (or any material which conducts electricity), the permittivity of space 46 in CCD 328 will be affected as chips 42A, 42B, 42C travel from the inlet 48 to outlet 49, resulting in temporary or transient decreases in the capacitance, C, of CCD 328 while the metallic chips are present between the inner cylinder 36 and outer cylinder 38. For example, the temporary presence of a relative large metallic chip 42A in space 46 would be expected to temporarily decrease the capacitance of CCD 328 by a first amount, and the temporary presence of a relatively small metallic chip 42C (e.g. fuzz) would be expected to temporarily decrease the capacitance of CCD 328 by a second amount which is less than the first amount.

In some embodiments, as metallic chips 42A, 42B, 42C pass through space 46 of CCD 328, the resulting decrease in the capacitance of CCD 28 will result in a corresponding temporary increase in the reactance of CCD 28, assuming the frequency of the voltage or current applied is kept constant. This property of CCD 328 may be advantageously used to detect the presence of metallic chips 42A, 42B, 42C between inner cylinder 36 and outer cylinder 38 of CCD 28.

In some embodiments, CCD 328 may form part of an electric circuit 334 which may include first output terminal 44A and second output terminal 44B together defining a single interface between CCD 328 and controller 32. As shown in FIG. 3B, the total impedance of CCD 328 together with chips 42A, 42B, 42C may be represented as a component with impedance Z. In some embodiments, an alternating current or voltage may be applied across CCD 328 and the voltage across CCD 328 may be measured by, or transmitted to, controller 32. The magnitude of the voltage drop across CCD 328 may serve as an output for controller 32 to use as an indication of whether or not a chip detection has occurred at CCD 328 and whether a notification 47 is warranted for further investigation and/or inspection and/or repair.

For example, controller 32 may be operable to store, in memory, data points over time of the capacitance of CCD 328 during operation of engine 10. Such data points may be analyzed for trends in capacitance changes. For example, a data model may be generated using one or more of linear regression, machine learning, neural networks, and the like, to identify subsequent anomalies in the data received at controller 32 based on the observed potential difference (and therefore the changes in capacitance of CCD 328). Spikes (or patterns of data more generally) in the potential difference across CCD 328 may be processed and interpreted as signifying the presence of metallic particles in a fluid line which are of sufficient size to be indicative of a deteriorating engine health condition (or warranting further inspection). Controller 32 may be further configured to interpret aberrations in the potential difference across CCD 328 which are not indicative of a change in capacitance above a threshold amount as being attributable to fuzz and other particles which might not be indicative of deteriorating engine health.

For example, if an AC voltage with a constant frequency is applied to circuit 334, in the absence of metallic chips 42A, 42B within CCD 328, a reference potential difference across CCD 328 may be established. As metallic chips 42A, 42B, 42C subsequently pass through CCD 328 in direction 50, the temporary presence of chips 42A, 42B, 42C may cause a temporary decrease in the capacitance of CCD 328, which will cause a temporary increase in reactance and total impedance, thereby resulting in a temporary increase or spike in the voltage across CCD 328 relative to the reference potential difference value V. In some embodiments, a threshold difference for the potential difference across CCD 328 relative to the reference potential difference in the absence of metallic chips 42A, 42B may be defined or otherwise set. When the difference in the voltage drop across CCD 328 exceeds the reference value by more than this threshold amount, controller 32 may be configured to sent an alert or notification 47 to draw attention to the possible need for maintenance or inspection for engine. In some embodiments, a controller 32 may be configured to detect spikes and anomalies in the potential difference across CCD 328 by comparing the potential difference to a data model based on historical recorded data for engine 10 (this data may be obtained from the engine 10 being monitored, and/or may be based on data obtained from other engines which are the same make and model as engine 10).

Accordingly, a chip detection at CCD 328 may be detected by way of a change in potential difference V across the cylindrical capacitor, which may be determined at controller 32 using a classifier or machine learning model configured to predict the presence of chips. Upon detection of the change in potential difference V that is determined to be indicative of a legitimate chip detection, controller 32 may initiate notification 47 which may alert a pilot of the aircraft and/or another interested party. Notification 47 may be visual (e.g., indicator light or message) or aural (e.g., tone or spoken message).

Figure 4:
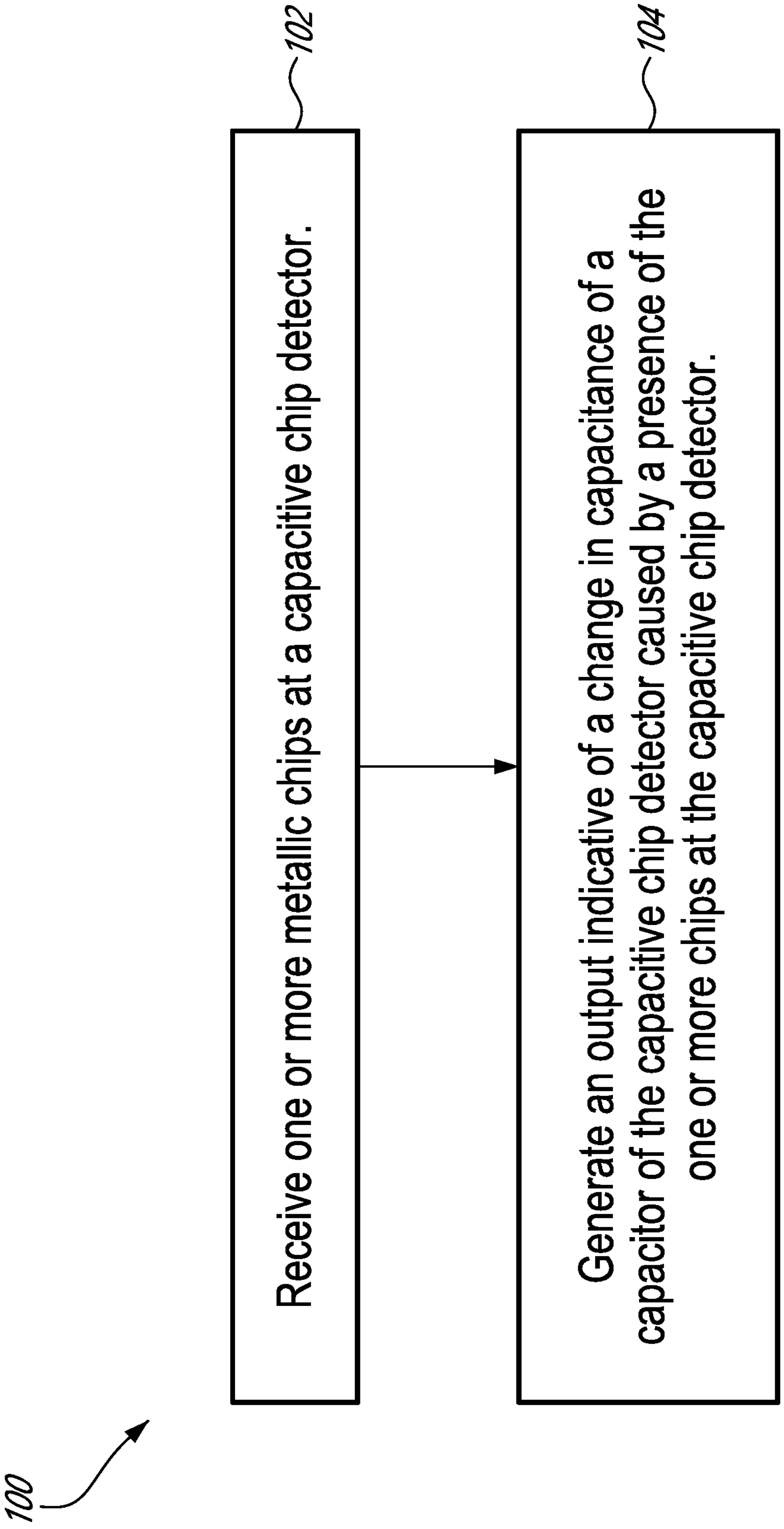
FIG. 4 is a flow diagram of a method of detecting metallic chips in engine fluid of an engine.

FIG. 4 is a flow diagram of method 100 of detecting metallic chips in engine fluid of an engine. Method 100 may be performed using, for example, CCD 28 described herein or using another CCD. Aspects of method 100 may be combined with other methods or steps described herein. Method 100 may also include aspects of system 30 and of CCD 28. In various embodiments, method 100 may include: receiving the engine fluid in the electric field between the first electric conductor (e.g., inner cylinder 36) and the second electric conductor (e.g., outer cylinder 38) (block 102); and using electric circuit 34 including the capacitor of the CCD 28, generating an output indicative of a change in capacitance of the capacitor caused by the arrival or presence of one or more chips between the first electric conductor and the second electric conductor (block 104).

In some embodiments of method 100, the output may be indicative of the capacitance of the CCD 28 having decreased sufficiently to be indicative of or associated with chip detection.

The embodiments described in this document provide non-limiting examples of possible implementations of the present technology. Upon review of the present disclosure, a person of ordinary skill in the art will recognize that changes may be made to the embodiments described herein without departing from the scope of the present technology.

What is claimed is:

1. A capacitive chip detector for detecting one or more first metallic chips exceeding a threshold size in engine fluid of an engine, the capacitive chip detector comprising:

a capacitor including:

a first electric conductor having a first polarity;

a second electric conductor having a second polarity opposite the first polarity, the first electric conductor being spaced apart from the second electric conductor; and an electric field between the first electric conductor and the second electric conductor;

an inlet for receiving the engine fluid between the first electric conductor and the second electric conductor;

an electric circuit including the capacitor, the electric circuit providing an output indicative of a change in capacitance of the capacitor caused by a presence of the one or more first metallic chips between the first electric conductor and the second electric conductor; and a strainer for collecting the first metallic chips between the first electric conductor and the second electric conductor, the strainer including one or more apertures sized to:

allow passage of second metallic chips smaller than the threshold size through the strainer; and prevent passage of the first metallic chips through the strainer.

2. The capacitive chip detector of claim 1, wherein the electric circuit provides the output based on a magnitude of a potential difference across the capacitor.

3. The capacitive chip detector of claim 2, wherein the electric circuit provides the output when the magnitude of the potential difference across the capacitor differs from a reference potential difference magnitude by more than a threshold amount.

4. The capacitive chip detector of claim 2, wherein the electric circuit provides the output when the magnitude of the potential difference across the capacitor is greater than a reference potential difference magnitude by more than a threshold amount.

5. The capacitive chip detector of claim 1, wherein the capacitor is a cylindrical capacitor where the first electric conductor is an inner cylinder and the second electric conductor is an outer cylinder surrounding the inner cylinder.

6. The capacitive chip detector of claim 1, comprising an outlet downstream of the capacitor for letting the engine fluid out of the capacitive chip detector a, the strainer being disposed between the inlet and the outlet.

7. An aircraft engine comprising:
- a lubrication system for distributing lubricating fluid to one or more lubrication loads; and
- a capacitive chip detector for detecting one or more metallic chips indicative of a deteriorating engine health carried by the lubricating fluid, the capacitive chip detector including:
  - a cylindrical capacitor including:
    - an electrically conductive inner cylinder having a first polarity;
    - an electrically conductive outer cylinder having a second polarity opposite the first polarity, the outer cylinder surrounding the inner cylinder and being radially spaced apart from the inner cylinder; and
    - an electric field between the inner cylinder and the outer cylinder;
  - an inlet configured to receive the lubricating fluid and the metallic chips between the inner cylinder and the outer cylinder;
  - an electric circuit including the cylindrical capacitor, the electric circuit providing an output indicative of a change in capacitance of the cylindrical capacitor caused by an arrival of one or more metallic chips between the inner cylinder and the outer cylinder; and
  - a strainer disposed downstream of the inlet for preventing the one or more metallic chips from exiting the capacitive chip detector.

8. The aircraft engine of claim 7, wherein the strainer includes a mesh sized to prevent passage of chips exceeding a threshold chip size.

9. The aircraft engine of claim 7, wherein;
- the one or more metallic chips are one or more first metallic chips exceeding a threshold size;
- the strainer comprises one or more apertures sized to:
  - permit passage of the lubricating fluid and of second metallic chips carried by the lubricating fluid and that are smaller than the threshold size through the strainer; and
  - to prevent passage of first metallic chips through the strainer.

10. The aircraft engine of claim 7, wherein the output includes a magnitude of a potential difference across the capacitor.

11. A method of detecting metallic chips in engine fluid of an aircraft engine using a capacitive chip detector including a capacitor defined by a first electric conductor having a first polarity and a second electric conductor having a second polarity opposite the first polarity, the first electric conductor being spaced apart from the second electric conductor, the method comprising:
- receiving the engine fluid carrying the metallic chips in an electric field between the first electric conductor and the second electric conductor;
- using an electric circuit including the capacitor, generating an output indicative of a change in capacitance of the capacitor caused by a presence of one or more of the metallic chips between the first electric conductor and the second electric conductor; and
- passing the engine fluid through a strainer within the capacitive chip detector, wherein:
  - the metallic chips are first metallic chips exceeding a threshold size;
  - the method includes:
    - permitting passage of second metallic chips carried by the engine fluid and that are smaller than the threshold size through the strainer and out of an outlet of the capacitive chip detector; and
    - preventing passage of the first metallic chips through the strainer and out of the outlet of the capacitive chip detector.

12. The method of claim 11, wherein the strainer includes one or more apertures sized to prevent passage of the first metallic chips exceeding the threshold size.

13. The method of claim 11, comprising removing the strainer from the capacitive chip detector to access the first metallic chips.

14. The method of claim 11, wherein the capacitor has a cylindrical configuration.

15. The method of claim 14, wherein generating the output based on a magnitude of a potential difference differing from a reference potential difference magnitude by more than a threshold amount.

* * * * *